United States Patent [19]

Neustadt

[11] Patent Number: 5,075,302
[45] Date of Patent: Dec. 24, 1991

[54] MERCAPTOACYL AMINOLACTAM ENDOPEPTIDASE INHIBITORS

[75] Inventor: Bernard R. Neustadt, West Orange, N.J.

[73] Assignee: Schering Corporation, Kenilworth, N.J.

[21] Appl. No.: 491,148

[22] Filed: Mar. 9, 1990

[51] Int. Cl.$^5$ .................. A61K 31/55; C07D 223/10
[52] U.S. Cl. .................. 514/211; 514/212; 514/213; 514/222.2; 514/224.2; 514/228.8; 514/230.5; 514/230.8; 514/299; 514/301; 514/302; 514/312; 514/327; 514/418; 514/424; 540/454; 540/455; 540/490; 540/488; 540/523; 540/524; 540/527; 546/114; 546/115; 546/112; 546/157; 546/244; 548/550; 548/452; 548/484
[58] Field of Search .................. 548/550, 452, 484; 546/244, 114, 115, 112, 157; 540/454, 455, 490, 488, 523, 524, 527; 514/211, 212, 213, 222.2, 224.2, 228.8, 230.5, 230.8, 299, 301, 302, 312, 327, 418, 424

[56] References Cited

U.S. PATENT DOCUMENTS

| | | | |
|---|---|---|---|
| 4,105,776 | 8/1978 | Ondetti et al. | 424/274 |
| 4,256,761 | 3/1981 | Suh et al. | 424/282 |
| 4,344,949 | 8/1982 | Hoefle et al. | 424/258 |
| 4,350,704 | 9/1982 | Hoefle et al. | 424/274 |
| 4,374,829 | 2/1983 | Harris et al. | 424/177 |
| 4,374,847 | 2/1983 | Gruenfeld | 424/274 |
| 4,410,520 | 10/1983 | Watthey | 424/244 |
| 4,462,943 | 7/1984 | Petrillo et al. | 260/112.5 R |
| 4,468,519 | 8/1984 | Krapcho | 548/409 |
| 4,470,972 | 9/1984 | Gold et al. | 424/177 |
| 4,470,973 | 9/1984 | Naterajan et al. | 424/177 |
| 4,508,729 | 4/1985 | Vincent et al. | 514/419 |
| 4,512,924 | 4/1985 | Attwood et al. | 260/243.3 |
| 4,513,009 | 4/1985 | Roques et al. | 514/513 |
| 4,555,506 | 11/1985 | Karanewsky et al. | 514/91 |
| 4,740,499 | 4/1988 | Olins | 514/13 |
| 4,774,256 | 9/1988 | Delaney et al. | 514/513 |
| 4,801,609 | 1/1989 | Haslanger et al. | 514/506 |

FOREIGN PATENT DOCUMENTS

| | | | |
|---|---|---|---|
| 38046 | 10/1981 | European Pat. Off. | 548/409 |
| 46953 | 3/1982 | European Pat. Off. | 514/299 |
| 50800 | 5/1982 | European Pat. Off. | 514/513 |
| 79022 | 5/1983 | European Pat. Off. | 514/513 |
| 79522 | 5/1983 | European Pat. Off. | 514/513 |
| 274234 | 7/1988 | European Pat. Off. | 514/513 |
| 2095682 | 10/1982 | United Kingdom | 514/513 |
| 2207351 | 2/1989 | United Kingdom | 514/513 |

OTHER PUBLICATIONS

Needleman et al., *N. Engl. J. Med.*, 314, 13 (1986), pp. 828–834.
Cantin et al., *Sci. Amer.*, 254 (1986), pp. 76–81.
Wyvratt et al., *Med. Res. Rev.*, 5, 4 (1985), pp. 483–531.
Miyamura et al., *J. Chem. Soc. Dalton Trans.*, (1987), pp. 1127–1187.

*Primary Examiner*—Robert T. Bond
*Attorney, Agent, or Firm*—Anita W. Magatti; James R. Nelson

[57] ABSTRACT

Mercaptoacyl aminolactam inhibitors of endopeptidases of the formula

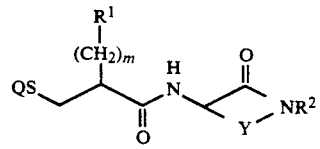

wherein Y is $-(CHR^5)_n(CR^3R^4)-$ or $-(CR^3R^4)_pX(CR^3R^4)_q-$,
wherein two substituents selected from the group consisting of $R^3$, $R^4$ and $R^5$, can form a benzene, cyclopentane or cyclohexane ring;
X is -O-, -S-, -SO- or -SO$_2$-;
Q is hydrogen or R$^6$CO-;
m is 1 or 2;
n is 1, 2, 3 or 4;
p is 1 or 2;
q is 2 or 3;
$R^1$ is lower alkyl, aryl or heteroaryl;
$R^2$ is hydrogen, lower alkyl, hydroxylower alkyl, lower alkoxylower alkyl, aryllower alkyl or heteroaryllower alkyl;
$R^3$ and $R^4$ are independently hydrogen, lower alkyl, aryllower alkyl or heteroaryllower alkyl;
$R^5$ is hydrogen, lower alkyl, aryllower alkyl, heteroaryllower alkyl, hydroxy, lower alkoxy, mercapto, or lower alkylthio; and $R^6$ is lower alkyl, aryl or heteroaryl, use of the compounds, alone or in combination with an ACE inhibitor or an ANF, in the treatment of cardiovascular disorders such as hypertension, congestive heart failure, edema and renal insufficiency, use of the compounds in the treatment of pain conditions, and pharmaceutical compositions containing said compounds are disclosed.

10 Claims, No Drawings

MERCAPTOACYL AMINOLACTAM ENDOPEPTIDASE INHIBITORS

BACKGROUND OF THE INVENTION

The present invention relates to mercaptoacyl aminolactam inhibitors of endopeptidases useful in the treatment of cardiovascular disorders and pain conditions.

Cardiovascular conditions which may be treated with compounds of the present invention include hypertension, congestive heart failure, edema and renal insufficiency.

Human hypertension is a disease of multiple etiologies. Included among these is a sodium and volume dependent low renin form of hypertension. Drugs that act to control one aspect of hypertension will not necessarily be effective in controlling another.

Enkephalin is a natural opiate receptor agonist which is known to produce a profound analgesia when injected into the brain ventricle of rats. Enkephalin is known to be inactivated by a group of naturally occurring enzymes known as enkephalinases or endopeptidases.

A variety of compounds known as endopeptidase inhibitors are useful as analgesics and/or in the treatment of hypertension. For example, European Patent Application 38,046 discloses enkephalinase inhibitors of the formula

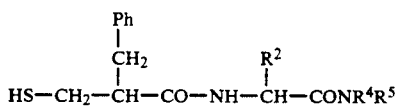

wherein $R^2$ is lower alkyl or methylthiomethyl, Ph is optionally substituted phenyl and $R^4$ and $R^5$ are hydrogen or alkyl.

U.S. Pat. No. 4,513,009 discloses alpha amino acid derivatives of the formula

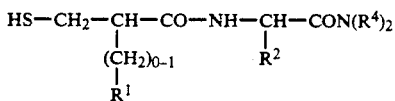

wherein $R^1$ can be alkyl, phenyl or thienyl, $R^2$ is preferably hydrogen, alkyl, benzyl or benzyloxyalkyl and $R^4$ can be alkyl or substituted alkyl. The compounds are said to have enkephalinase inhibiting and hypotensive activity. U.S. Pat. No. 4,740,499 discloses the use of thiorphan (a compound within the scope of U.S. Pat. No. 4,513,009 but having a terminal carboxy group) to enhance the activity of an atrial peptide.

U.S. Pat. No. 4,801,609 discloses mercaptoacylamino acids of the formula

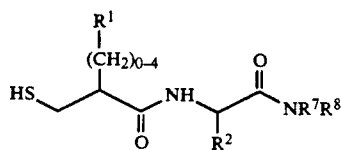

wherein $R^1$ can be aryl or heteroaryl, $R^2$ can be alkylthioalkyl or alkoxyalkyl and $R^7$ and $R^8$ can each be substituted alkyl or together can form a ring.

U.S. Pat. No. 4,774,256 discloses analgesic enkephalinase inhibitors of the formula

wherein $R^2$, $R^3$, $R^7$ and $R^8$ can be alkyl, arylalkyl or heteroarylalkyl, or $R^7$ and $R^8$ can form a ring, and n can be 1-15. German Patent Application 3,819,539 discloses a variety of compounds, including those of a scope similar to the '256 patent wherein $R^7$ and $R^8$ form a ring; the compounds are said to be diuretics, natriuretics and blood pressure lowering agents.

It is known that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homostasis", *N. Engl. J. Med.*, 314, 13 (1986) pp. 828–834, and M. Cantin et al in "The Heart as an Endocrine Gland", *Scientific American*, 254 (1986) pg. 76–81.

Angiotensin converting enzyme (ACE) inhibitors are another class of drugs known to be effective in treating some types of hypertension. ACE inhibitors are useful in blocking the rise in blood pressure caused by increases in vascular resistance and fluid volume due to the formation of angiotensin II from angiotensin I. For a review of ACE inhibitors, see M. Wyvratt et al., "Recent Developments in the Design of Angiotensin Converting Enzyme Inhibitors" in *Med. Res. Rev.*, 5, No. 4 (1985) pp. 483–531.

SUMMARY OF THE INVENTION

Novel compounds of the present invention are represented by the formula

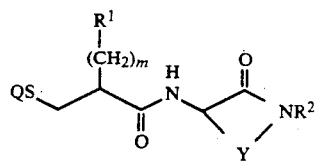

wherein Y is -(CHR$^5$)$_n$(CR$^3$R$^4$)- or -(CR$^3$R$^4$)$_p$X(CR$^3$R$^4$)$_q$-, wherein two substituents selected from the group consisting of R$^3$, R$^4$ and R$^5$, together with the carbons to which the substituents are attached, when the substituents are present on adjacent carbon atoms, can form a benzene, cyclopentane or cyclohexane ring;

X is -O-, -S-, -SO- or -SO$_2$-;

Q is hydrogen or R$^6$CO-;

m is 1 or 2;

n is 1, 2, 3 or 4;

p is 1 or 2;

q is 2 or 3;

R$^1$ is lower alkyl, aryl or heteroaryl;

R$^2$ is hydrogen, lower alkyl, hydroxylower alkyl, lower alkoxylower alkyl, aryllower alkyl or heteroaryllower alkyl;

R[3] and R[4] are independently hydrogen, lower alkyl, aryllower alkyl or heteroaryllower alkyl;

R[5] is hydrogen, lower alkyl, aryllower alkyl, heteroaryllower alkyl, hydroxy, lower alkoxy, mercapto or lower alkylthio; and R[6] is lower alkyl, aryl or heteroaryl.

A preferred group of compounds is that wherein Y is $-(CHR^5)_n(CR^3R^4)-$, especially wherein R[3], R[4] and R[5] are each hydrogen and n is 2 or 3, i.e., Y is propylene or butylene. Another preferred group of compounds is that wherein R[1] is phenyl or lower alkyl-substituted phenyl. A preferred value for m is 1. Q is preferably hydrogen or acetyl. R[2] is preferably hydrogen.

Another group of preferred compounds of formula I is that wherein Q is hydrogen or acetyl, R[1] is phenyl or loweralkyl-substituted phenyl, m is 1 and R[2] is hydrogen; especially preferred are compounds of this group wherein Y is propylene or butylene.

The invention also relates to the treatment of cardiovascular diseases with a combination of a mercaptoacyl aminolactam of the present invention and an atrial natriuretic factor (ANF) or with a combination of a mercaptoacyl aminolactam of the present invention and an ACE inhibitor.

Other aspects of the invention relate to pharmaceutical compositions comprising a mercaptoacyl aminolactam of this invention, alone or in combination with an ANF or an ACE inhibitor, and to methods of treatment of cardiovascular diseases comprising administering a mercaptoacyl aminolactam of this invention, alone or in combination with an ANF or an ACE inhibitor, to a mammal in need of such treatment.

Still another aspect of this invention relates to a method of treating pain conditions by administering a mercaptoacyl aminolactam of this invention, thereby inhibiting the action of endopeptidases in a mammal and eliciting an analgesic effect. Analgesic pharmaceutical compositions comprising said mercaptoacyl aminolactam compounds are also contemplated.

DETAILED DESCRIPTION

As used herein, the term "alkyl" means straight or branched lower alkyl chains of 1 to 6 carbon atoms and "alkoxy" similarly means lower alkoxy chains of 1 to 6 carbon atoms.

"Aryl" means phenyl, naphthyl, or a phenyl or naphthyl ring substituted with 1-3 substituents selected from the group consisting of alkyl, hydroxy, alkoxy, halo, trifluoromethyl, phenyl, phenoxy and phenylthio.

"Heteroaryl" means aromatic groups having 5 or 6 ring members wherein 1-2 ring members are independently selected from the group consisting of oxygen, nitrogen and sulfur and wherein 1-3 carbon ring members may be substituted with substituents as defined above for aryl. Examples of heteroaryl groups are furanyl, thienyl, pyrrolyl and pyridyl.

In the compounds of formula 1, the variable Y is attached in the lactam ring as follows:

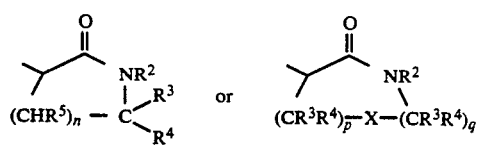

All positional isomers of the aryl and heteroayl groups are contemplated, e.g. 2-pyridyl and 3-pyridyl, α-naphthyl and β-naphthyl.

Halo means fluoro, chloro, bromo or iodo radicals.

Compounds of formula I have at least one asymmetrical carbon atom and therefore include various stereoisomers. The invention includes all such isomers both in pure form and in admixture, including racemic mixtures.

An aspect of the present invention described above relates to the combination of a compound of formula I with an ANF. As indicated by Needleman et al., a number of ANF have been isolated so far, all having the same core sequence of 17 amino acids within a cysteine disulfide bridge, but having different N-termini lengths. These peptides represent N-terminal truncated fragments (21-48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occurring ANF's also have been found to have comparable biological activity. Examples of ANF's contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence of each of the above wherein Met 12 is Ile. See Table 1 for a comparison of the peptides.

TABLE 1

HUMAN PEPTIDE

AP 33
LeuAlaGlyProArgSerLeuArgArgSerSerCys-SPheGlyGlyArgMetAspArgIleGlyAlaGlnSerGlyLeuGlyCys-SAsnSerPheArgTyr

AP 28    Ser ———————————————————————— Tyr

AP 26    Arg ———————————————————————— Tyr

AP 25    Arg ———————————————————————— Tyr

AP 24    Ser ———————————————————————— Tyr

AP 23    Ser ———————————————————————— Arg

TABLE 1-continued

| HUMAN PEPTIDE | | |
|---|---|---|
| AP 21 | Ser———————————————————————————Ser | |

*Ile in the rat peptide

Another aspect of the invention is the administration of a combination of an ACE inhibitor and a compound of formula I.

Examples of ACE inhibitors are those disclosed in the article by Wyvratt et al., cited above, and in the following U.S. patents: U.S. Pat. Nos. 4,105,776, 4,468,519, 4,555,506, 4,374,829, 4,462,943, 4,470,973, 4,470,972, 4,350,704, 4,256,761, 4,344,949, 4,508,729, 4,512,924, 4,410,520 and 4,374,847, all incorporated herein by reference; and the following foreign patents or published patent applications:

British Specification No. 2095682 published Oct. 6, 1982 discloses N-substituted-N-carboxyalkylcarbonyl amino carboxyl alkyl glycine derivatives which are said to be angiotensin converting enzyme inhibitors and have the formula

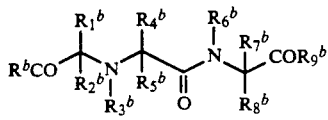

either (A) $R^b$ and $R_9^b$ are OH, 1-6C alkoxy, 2-6C alkonyloxy, di-(1-6C alkyl)amino-(1-6C) alkoxy, 1-6C hydroxy alkoxy, acylamino-(1-6C)alkoxy, acyloxy-(1-6C)alkoxy, aryloxy, aryloxy-(1-6C)alkoxy, $NH_2$, mono- or di-(1-6C alkyl)amino, hydroxy amino or aryl-(1-6C)alkylamino; $R_1^b$-$R_5^b$, $R_7^b$ and $R_8^b$ are 1-20C alkyl, 2-20C alkonyl, 2-20C alkynyl, aryl, aryl-(1-6C) alkyl having 7-12C or heterocyclyl-(1-6C)alkyl having 7-12C;

$R_6^b$ is cycloalkyl, polycycloalkyl, partly saturated cycloalkyl or polycycloalkyl, cycloalkyl-(1-6C)alkyl having 3-20C, 6-10C aryl, aryl-(1-6C)alkyl, aryl-(2-6C)alkenyl or aryl-(2-6C) alkynyl; or $R_2^b$ and $R_3^b$ together with the C and N atoms to which they are attached or $R_3^b$ and $R_5^b$ together with the N and C atoms to which they are attached form an N-heterocycle containing 3-5C or 2-4C and a S atom;

all alkyl, alkonyl and alkynyl are optionally substituted by OH, 1-6C alkoxy, thio(sic), 1-6C alkylthio, $NH_2$, mono- or di(1-6C alkyl)amino, halogen or $NO_2$;

all 'cycloalkyl' groups (including poly and partially unsaturated) are optionally substituted by halogen, 1-6C hydroxy alkyl, 1-6C alkoxy, amino-(1-6C alkyl)amino, di-(1-6C alkyl)amino, SH, 1-6C alkylthio, $NO_2$ or $CF_3$; and aryl groups are optionally substituted by OH, 1-6C alkoxy, $NH_2$, mono- or di-(1-6C alkyl) amino, SH, 1-6C alkylthio, 1-6C hydroxy alkyl, 1-6C aminoalkyl, 1-6C thioalkyl, $NO_2$, halogen, $CF_3$, $OCH_2O$, ureido or guanidino; or (B) $R^b$ and $R_9^b$ are H or 1-6C alkoxy; $R_1^b$ and $R_2^b$ are H, 1-6C alkyl, aryl-(1-6C) alkyl having 7-12C or heterocyclyl-(1-6C) alkyl having 6-12C;

$R_3^b$-$R_5^b$, $R_7^b$ and $R_8^b$ are H or 1-6C alkyl; $R_6^b$ is cycloalkyl, polycycloalkyl, partly saturated cycloalkyl or polycycloalkyl, cycloalkyl-(1-6C) alkyl having 3-20C, aryl or aryl-(1-6C) alkyl; and aryl has 6-10C and is optionally substituted by 1-6C alkyl, 2-6C alkonyl, 2-6C alkynyl, OH, 1-6C alkoxy, $NH_2$, mono- or di-(1-6C alkyl) amino, SH, 1-6C alkylthio, 1-6C hydroxy alkyl, 1-6C aminoalkyl, 1-6C thioalkyl, $NO_2$, halogen, $CF_3$, $OCH_2O$, ureido or guanidino;

European Patent Application 0 050 800 published May 5, 1982 discloses carboxy alkyl dipeptides derivatives which are said to be angiotensin converting enzyme inhibitors and have the formula

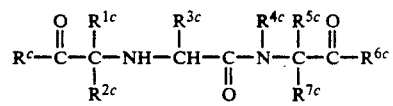

or a pharmaceutically acceptable salt thereof, wherein $R^c$ and $R^{6c}$ are the same or different and are hydroxy, lower alkoxy, lower alkonyloxy, dilower alkylamino lower alkoxy, acylamino lower alkoxy, acyloxy lower alkoxy, aryloxy, aryllower alkoxy, amino, lower alkylamino, dilower alkylamino, hydroxy amino, aryllower alkylamino, or substituted aryloxy or substituted aryl-lower alkoxy wherein the substituent is methyl, halo or methoxy; $R^{1c}$ is hydrogen, alkyl of from 1 to 10 carbon atoms, substituted lower alkyl wherein the substituent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carboxyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2c}$ and $R^{7c}$ are the same or different and are hydrogen or lower alkyl; $R^{3c}$ is hydrogen, lower alkyl, phenyl lower alkyl, aminoethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4c}$ and $R^{5c}$ are the same or different and are hydrogen, lower alkyl or $Z^c$, or $R^{4c}$ and $R^{5c}$ taken together form a group represented by $Q^c$, $U^c$, $V^c$, $Y^c$, $D^c$ or $E^c$, wherein; $Z^c$ is

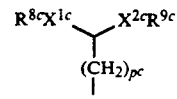

wherein $X^{1c}$ and $X^{2c}$ independent of each other are O, S or $CH_2$, $R^{8c}$ and $R^{9c}$ independent of each other are lower alkyl, lower alkonyl, lower alkynyl, cycloalkyl having 3 to 8 carbon atoms, hydroxy lower alkyl, or $-(CH_2)_{n^c}Ar^c$, wherein $n^c$ is 0, 1, 2 or 3 and $Ar^c$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8c}$ and $R^{9c}$ taken together form a bridge $W^c$, wherein $W^c$ is a single bond or a methylene bridge or a substituted methylene bridge when at least one of $X^{1c}$ and $X^{2c}$ is methylene, or $W^c$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^c$ is 0, 1 or 2; with the proviso that at least one of $R^{4c}$ and $R^{5c}$ is $Z^c$, with the proviso that if $R^{4c}$ is $Z^c$ and $p^c$ is 0 then $X^{1c}$ and $X^{2c}$ must both be methylene, and with the proviso that if $X^{1c}$ and $X^{2c}$ are both methylene then $R^{8c}$ and $R^{9c}$ must form an alkylene bridge $W^c$;

$Q^c$ is

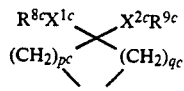

wherein $R^{8c}$, $R^{9c}$, $X^{1c}$ and $X^{2c}$ are as defined above, $p^c$ is 0, 1 or 2, $q^c$ is 0, 1 or 2, with the proviso that the sum of $p^c$ and $q^c$ must be 1, 2 or 3, with the proviso that if $p^c$ is 0 then $X^{1c}$ and $X^{2c}$ must be methylene, and with the proviso that if $X^{1c}$ and $X^{2c}$ are methylene then $R^{8c}$ and $R^{9c}$ taken together form a bridge $W^c$, wherein $W^c$ is as defined above;

$V^c$ is

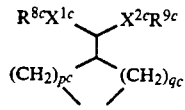

wherein $R^{8c}$, $R^{9c}$, $X^{1c}$ and $X^{2c}$ are as defined above, $p^c$ is 0, 1 or 2 and $q^c$ is 0, 1 or 2, with the proviso that the sum of $p^c$ and $q^c$ is 1, 2 or 3, with the proviso that if $X^{1c}$ and $X^{2c}$ are $CH_2$ then $R^{8c}$ and $R^{9c}$ taken together form a bridge $W^c$, wherein $W^c$ is as defined above;

$U^c$ is

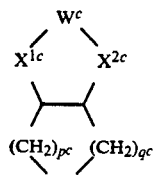

wherein $W^c$ is as defined above (except that $W^c$ may also be a methylene bridge when $X^{1c}$ and $X^{2c}$ are oxygen or sulfur), $X^{1c}$ and $X^{2c}$ are as defined above, $p^c$ is 0, 1 or 2, $q^c$ is 0, 1 or 2, with the proviso that the sum of $p^c$ and $q^c$ is 1 or 2, and with the proviso that if $p^c$ is 0, $X^{1c}$ must be $CH_2$;

$Y^c$ is

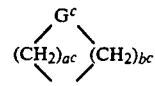

wherein $G^c$ is oxygen, sulfur or $CH_2$, $a^c$ is 2, 3 or 4 and $b^c$ is 1, 2, 3, 4 or 5, with the proviso that the sum of $a^c$ and $b^c$ is 5, 6 or 7 or $G^c$ is $CH_2$, $a^c$ is 0, 1, 2 or 3, $b^c$ is 0, 1, 2 or 3 with the proviso that the sum of $a^c$ and $b^c$ is 1, 2 or 3, with the proviso that the sum of $a^c$ and $b^c$ may be 1, 2 or 3 only if $R^{1c}$ is lower alkyl substituted with aralkylthio or aralkyloxy;

$D^c$ is

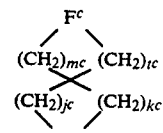

wherein $F^c$ is O or S, $j^c$ is 0, 1 or 2 and $k^c$ is 0, 1 or 2, with the proviso that the sum of $j^c$ and $k^c$ must be 1, 2 or 3, and $m^c$ is 1, 2 or 3 and $t^c$ is 1, 2 or 3, with the proviso that the sum of $m^c$ and $t^c$ must be 2, 3 or 4;

$E^c$ is

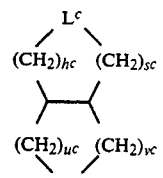

wherein $L^c$ is O or S, $u^c$ is 0, 1 or 2 and $v^c$ is 0, 1 or 2, with the proviso that the sum of $u^c$ and $v^c$ must be 1 or 2, and $h^c$ is 1 or 2 and $s^c$ is 1 or 2, with the proviso that the sum of $h^c$ and $s^c$ must be 2 or 3;

European Patent Application 0 079 522 published May 25, 1983 discloses N-carboxymethyl(amidino)lysylprolyl compounds which are said to be angiotensin converting enzyme inhibitors and have the formula where

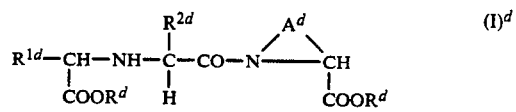

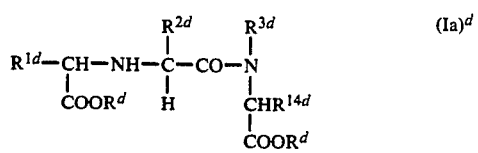

wherein:
$R^d$ and $R^{2d}$ are independently hydrogen; loweralkyl; aralkyl; or aryl;
$R^{1d}$ is hydrogen; branched or straight chain $C_{1-12}$ alkyl and alkonyl; $C_3-C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

$$-N\underset{COOR^d}{\overset{A^d}{<}}CH \quad \text{is} \quad -N\underset{R^dOOC}{\overset{X^d-Y^d}{<}}(CH)_{n^d},\ R^{4d}$$

$$-N\underset{R^dOOC}{\overset{W^d}{<}}\underset{Z^d}{\bigcirc}R^{6d} \quad \text{or}$$

$$-N\underset{COOR^d}{\overset{W^d}{<}}\underset{Z^d}{\bigcirc}\ )_{nd}$$

where:

$X^d$ and $Y^d$ taken together are -CH$_2$-CH$_2$-;

$$-\underset{R^{5d}}{CH}-S-;\ -\underset{O}{\overset{O}{\|}}C-CH_2-;\ -CH_2-\overset{O}{\overset{\|}{C}}-;\ -\overset{O}{\overset{\|}{C}}-O-;$$

$$-\overset{O}{\overset{\|}{C}}-S-;\ -CH_2-\underset{OR^{4d}}{CH}-;\ -\overset{O}{\overset{\|}{C}}-\underset{R^{4d}}{N}-;\ \text{or}\ -CH_2-\underset{R^{4d}}{C}-R^{5d};$$

$R^{4d}$ is hydrogen; loweralkyl; aryl; substituted aryl;
$R^{5d}$ is hydrogen; loweralkyl; aryl or substituted aryl;
$n^d$ is 1 to 3;
$W^d$ is absent; -CH$_2$-; or $$-\overset{O}{\overset{\|}{C}}-;$$

$Z^d$ is -(CH$_2$)$_{m^d}$, where m$^d$ is 0 to 2, provided that m$^d$ may not be 0 and W$^d$ may not be absent at the same time; and
$R^{6d}$ is hydrogen; loweralkyl; halo; or OR$^{4d}$;
$R^{2d}$ is —(CH$_2$)$_{r^d}$—B$^d$—(CH$_2$)$_{s^d}$—NR$^{7d}$R$^{15d}$
where
r$^d$ and s$^d$ are independently 0 to 3;
B$^d$ is absent; -O-; -S-; or -NR$^{8d}$;
where R$^{8d}$ is hydrogen; loweralkyl; alkanoyl; or aroyl; and $$-\overset{NR^{11d}}{\overset{\|}{C}}-R^{9d};\ -\overset{NR^{11d}}{\overset{\|}{C}}-NHR^{10d};\ \text{or}\ -\overset{N-J^d}{\overset{\|}{C}}\!\!\!+\!\!R^{12d}$$

where
$R^{9d}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10d}$ is hydrogen; loweralkyl; aryl; or amidino;
$R^{11d}$ hydrogen; loweralkyl; cyano; amidino; aryl; aroyl; loweralkanoyl;

$$-\overset{O}{\overset{\|}{C}}-NHR^{13d};$$

$$-\overset{O}{\overset{\|}{C}}-OR^{13d};\ -NO_2;\ -SO_2NH_2;$$

or SO$_2$R$^{13d}$;
$R^{12d}$ is hydrogen; loweralkyl; halo; aralkyl; amino; cyano; mono- or diloweralkylamino; or OR$^{4d}$;
$R^{13d}$ is hydrogen; loweralkyl; or aryl;
$R^{15d}$ is hydrogen; lower alkyl; aralkyl; or aryl;

$$-\overset{N-J^d}{\overset{\|}{C}}\!\!\!+\!\!R^{12d}\\ -C-K^d$$

constitute a basic heterocycle of 5 or 6 atoms or benzofused analogs thereof and optionally containing 1-3 N atoms, an oxygen, a sulfur, an S=O, or an SO$_2$ group optionally substituted by amino, lower alkyl amino, diloweralkyl amino, lower alkoxy, or aralkyl groups;
$R^{3d}$ is C$_{3-8}$ cycloalkyl and benzofused C$_{3-8}$ cycloalkyl; perhydrobenzofused C$_{3-8}$ cycloalkyl; aryl; substituted aryl; heteraryl; substituted heteroaryl;
$R^{14d}$ is hydrogen or loweralkyl; and, a pharmaceutically acceptable salt thereof;

European Patent 79022 published May 18, 1983 discloses N-amino acyl-azabicyclooctane carboxylic acid derivatives which have the formula $$X^e-\underset{Z^e}{\overset{Y^e}{\underset{|}{C}}}-CH_2-\underset{COOR_2^e}{CH}-NH-\underset{R_1^e}{CH}-CO-N\underset{HOOC}{\bigcirc}$$

hydrogen atoms at ring positions 1 and 5 are cis to each other and the 3-carboxy group has the endo orientation;
$R_1^e$ is H, allyl, vinyl or the side chain of an optionally protected naturally occurring α-amino acid;
$R_2^e$ is H, 1-6C alkyl, 2-6C alkonyl or aryl(1-4C alkyl);
$Y^e$ is H or OH and $Z^e$ is H, or $Y^e$ and $Z^e$ together oxygen;
$X^e$ is 1-6C alkyl, 2-6C alkonyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl);

European Patent 46953 published Mar. 10, 1982 discloses N-amino acyl-indoline and tetrahydro isoquinoline carboxylic acids which are angiotensin coverting enzyme inhibitors and have the formula

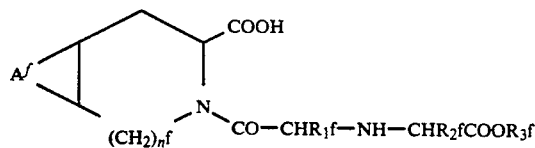

$n^f$ is 0 or 1;

is a benzene or cyclohexane ring:

$R_1{}^f$ and $R_2{}^f$ are each 1-6C alkyl, 2-6C alkonyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1{}^f$ and $R_2{}^f$ groups are optionally substituted, $R_3{}^f$ is H, 1-6C alkyl, 2-6C alkonyl or 7-14C aralkyl.

The following Table II lists ACE inhibitors preferred for use in the combination of this invention.

TABLE II
PREFERRED ACE INHIBITORS $$\begin{array}{ccc} COOR^1 & R^2 & O \\ | & | & \| \\ R-CH-NH-CH-C-R^3 \end{array}$$

| | R | $R_1$ | $R_2$ | $R_3$ |
|---|---|---|---|---|
| spirapril | $C_6H_5CH_2CH_2-$ | Et | $CH_3$ | (S,S-dithiolane-prolyl) |
| enalapril | $C_6H_5CH_2CH_2-$ | Et | $CH_3$ | prolyl |
| ramipril | $C_6H_5CH_2CH_2-$ | Et | $CH_3$ | (cyclopentane-fused prolyl) |
| perindopril | $CH_3CH_2CH_2$ | Et | $CH_3$ | (cyclohexane-fused prolyl) |
| indolapril | $C_6H_5CH_2CH_2-$ | Et | $CH_3$ | (cyclohexane-fused prolyl) |
| lysinopril | $C_6H_5CH_2CH_2-$ | H | $NH_2(CH_2)_4-$ | prolyl |
| quinapril | $C_6H_5CH_2CH_2-$ | Et | $CH_3$ | (benzo-fused prolyl) |
| pentopril (NH = $CH_2$) | $CH_3$ | Et | $CH_3$ | (benzo-fused prolyl) |

TABLE II-continued
PREFERRED ACE INHIBITORS

| | | | | |
|---|---|---|---|---|
| cilazapril | C₆H₅CH₂CH₂— | H | R₂ O<br>\| \|\|<br>CH—C—R₃= | 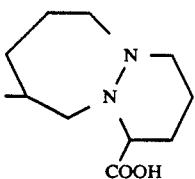 |

$$RS-CH_2-CH_2-\overset{\overset{CH_3}{\|}}{C}-R^2$$
$$\phantom{RS-CH_2-CH_2-}\overset{O}{\|}$$

| | R | R₂ |
|---|---|---|
| captopril | H | prolyl |
| zofenopril | C₆H₅CO— | 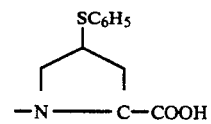 |
| pivalopril | (CH₃)₃C—C(=O)— | —N—CH₂—COOH (cyclopentyl) |

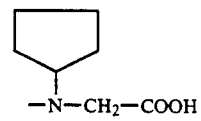

| | R | R¹ | R² |
|---|---|---|---|
| fosinopril | C₆H₅—(CH₂)₄— | (CH₃)₂<br>\|<br>CH<br>\|<br>—CH—O—C(=O)—CH₂CH₃ | C₆H₅— |

The compounds of the present invention can be produced by methods known to those skilled in the art, for example by the methods described below. Reactive groups not involved in the condensations described below, e.g., mercapto, etc., may be protected by methods standard in peptide chemistry prior to the coupling reactions and subsequently deprotected to obtain the desired products. In the formulae in the following description of the processes, Q, R¹, R², Y and m are as defined above for formula I, including suitable protection where appropriate.

An acid of formula II can be condensed with an aminolactam of formula III:

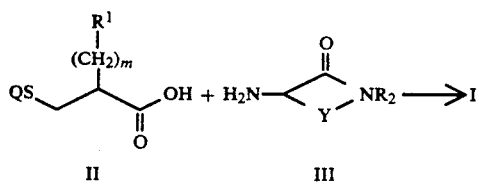

This reaction is well known from peptide chemistry. The reaction can be carried out in the presence of a condensing agent such as 1-(3-dimethylaminopropyl)-3-ethyl-carbodiimide hydrochloride (DEC), dicyclohexyl-carbodiimide (DCC), diphenylphosphoryl azide (DPPA) or N,N-disuccinimidyl carbonate in an inert solvent such as dimethylformamide. While, as mentioned above, reactive groups are protected before the coupling reaction is carried out, the carboxy group of compound II can be activated via the intermediacy of an active ester such as that derived from 1-hydroxybenzotriazole, the mixed anhydride (derived from a chlorocarbonic acid ester), or the azide.

Alternatively, a propionic acid of formula II may be reacted with thionyl chloride to prepare the corresponding propionyl chloride, which may then be reacted with an aminolactam of formula III in an inert solvent such as acetonitrile in the presence of a base such as triethylamine to obtain a compound of formula I.

It is evident that a compound of formula I obtained by the above process can be transformed into another compound of formula I by methods known in the art, e.g. a compound wherein Q is acetyl may be deprotected to obtain a compound wherein Q is hydrogen by treating with sodium hydroxide, then acidifying with HCl.

The starting compounds of formula II and III are known compounds and/or can be prepared according to known methods. See for example, *J. Chem. Soc.*

Dalton Trans., 1987, p. 1127, for preparing lactams of formula III.

We have found that the novel compounds of the present invention are effective in treating cardiovascular disorders such as congestive heart failure, edema, renal insufficiency and various types of hypertension, particularly volume expanded hypertension. These novel compounds enhance both the magnitude and duration of the antihypertensive and natriuretic effects of endogenous ANF. Administration of a combination of a mercaptoacyl aminolactam and an ACE inhibitor provides an antihypertensive and anticongestive heart failure effect greater than either the mercaptoacyl aminolactam or ACE inhibitor alone. Administration of a combination of a mercaptoacyl aminolactam of formula I and an exogenous ANF or ACE inhibitor is therefore particularly useful in treating hypertension or congestive heart failure.

In addition to the compound aspect, the present invention therefore also relates to treating cardiovascular disorders with a mercaptoacyl aminolactam of formula I or with a mercaptoacyl aminolactam of formula I in combination with an ANF or an ACE inhibitor, which methods comprise administering to a mammal in need of such treatment an amount of the mercaptoacyl aminolactam or an amount of a combination of a mercaptoacyl aminolactam and ANF or ACE inhibitor effective to treat hypertension, congestive heart failure, edema or renal insuffiency. The drug or combination of drugs is preferably administered in a pharmaceutically acceptable carrier, e.g. for oral or parenteral administration. The combinations of drugs may be co-administered in a single composition, or components of the combination therapy may be administered separately. Where the components are administered separately, any convenient combination of dosage forms may be used, e.g. oral mercaptoacyl aminolactam/oral ANF, oral mercaptoacyl aminolactam/parenteral ACE inhibitor, parenteral mercaptoacyl aminolactam/oral ANF, parenteral mercaptoacyl aminolactam/parenteral ACE inhibitor.

When the components of a combination of a mercaptoacyl aminolactam and an ANF are administered separately, it is preferred that the mercaptoacyl aminolactam be administered first.

The present invention also relates to a pharmaceutical composition comprising a mercaptoacyl aminolactam for use in treating hypertension, congestive heart failure, edema or renal insufficiency, to a pharmaceutical composition comprising both a mercaptoacyl aminolactam and an ANF and to a pharmaceutical composition comprising both a mercaptoacyl aminolactam and an ACE inhibitor.

The antihypertensive effect of mercaptoacyl aminolactams was determined according to the following procedure:

Male Sprague Dawley rats weighing 100–150 g were anesthetized with ether and the right kidney was removed. Three pellets containing DOC acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17–30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or mercaptoacyl aminolactam and blood pressure was monitored for the next 4 hours.

A similar procedure can be used to determine the effect of mercaptoacyl aminolactam in combination with ACE inhibitors.

The antihypertensive effect of mercaptoacyl aminolactams in combination with ANF can be determined according to the following procedures:

Male spontaneously hypertensive rats (SHR), 16–18 weeks old, 270–350 g, are anesthetized with ether and the abdominal aorta is cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 ml/hr. Animals are allowed a 90-min equilibration period. The animals first undergo a challenge with an ANF such as atriopeptin II (AP II) or AP28 30 $\mu$g/kg iv and at the end of 60 min. are treated with drug vehicle or a mercaptoacyl aminolactam subcutaneously. A second ANF challenge is administered 15 min. later and blood pressure is monitored for the next 90 min.

The antihypertensive effect in SHR of mercaptoacyl aminolactams and ACE inhibitors, alone and in combination, can be determined as follows:

Animals are prepared for blood pressure measurement as described above. After stabilization, animals are dosed subcutaneously or orally with test drugs or placebo and blood pressure is monitored for the next 4 hr.

The compounds having structural formula I have also been found to inhibit the activity of enzymes designated enkephalinases. The compounds are particularly useful for the inhibition of enkephalinase A, which is derived from the striata of both rats and humans. In vitro tests, using test procedures for enkephalinase A inhibition well known to those skilled in the art, selected compounds having structural formula I have been found to inhibit the activity of the aforementioned enzyme. Therefore, the present invention also relates to a method of inhibiting the action of enkephalinases in a mammal thereby to elicit an analgesic effect with a compound of formula I, and to analgesic pharmaceutical compositions comprising compounds of formula I.

The compositions of this invention comprise a mercaptoacyl aminolactam or a mercaptoacyl aminolactam and an ANF or a mercaptoacyl aminolactam and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily dose of the compound or combinations of this invention for treatment of hypertension, congestive heart failure, edema or renal insufficiency is as follows: for mercaptoacyl aminolactams alone the typical dosage is 1 to 100 mg/kg of mammalian weight per day administered in single or divided dosages; for the combination of mercaptoacyl aminolactam and an ANF, the typical dosage is 1 to 100 mg of mercaptoacyl aminolactam/kg mammalian weight per day in single or divided dosages plus 0.001 to 0.1 mg ANF/kg of mammalian weight per day, in single or divided dosages, and for the combination of mercaptoacyl aminolactam and an ACE inhibitor, the typical dosage is 1 to 100 mg of mercaptoacyl aminolactam/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension, congestive heart failure, edema or renal insufficiency, the compounds or combinations of this invention may be administered to patients in a dosage range as follows: for treatment with mercaptoacyl aminolactams alone, about 10 to about 500 mg per dose given 1 to 4 times a day, giving a total daily dose of about 10 to 2000 mg per day; for the combination of mercaptoacyl aminolactam and ANF, about 10 to about 500 mg mercaptoacyl aminolactam per dose given 1 to 4 times a day and about 0.001 to about 1 mg ANF given 1 to 6 times a day (total daily dosage range of 10 to 2000 mg day and 0.001 to 6 mg/day, respectively); and for the combination of a mercaptoacyl aminolactam and an ACE inhibitor, about 10 to about 500 mg mercaptoacyl aminolactam per dose given 1 to 4 times a day and about 5 to about 50 mg ACE inhibitor given 1 to 3 times a day (total daily dosage range of 10 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

To produce an analgesic effect, compounds of this invention will be administered in a dosage range of from about 1 to about 100 mg/kg. The doses are to be administered at intervals of from 3 to 8 hours. However, the quantity and frequency of dosage will depend upon such factors as the severity of the pain, the general physical condition of the patient, the age and weight of the patient, and other factors recognized by the skilled clinician.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene gylcol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Since the present invention relates to treatment of hypertension or congestive heart failure with a combination of active ingredients wherein said active ingredients may be administered separately, the invention also relates to combining separate pharmaceutical compositions in kit form. That is, two kits are contemplated, each combining two separate units: a mercaptoacyl aminolactam pharmaceutical composition and an ANF pharmaceutical composition in one kit and a mercaptoacyl aminolactam pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are examples of methods of preparing compounds of formula I.

EXAMPLE 1

3(S)-[2-ACETYLTHIOMETHYL-3-PHENYLPROPIONYL]AMINO-ε-CAPROLACTAM

Combine 3(S)-amino-ε-caprolactam (1.00 g, 7.8 mmol) and triethylamine (0.87 g, 8.6 mmol) in acetonitrile (40ml) and H$_2$O (20 ml). Add dropwise 2-acetylthiomethyl-3-phenylpropionyl chloride. After 30 min, add 1.0N HCl (13 ml), extract with ethyl acetate (EtOAc), dry and concentrate. Chromatograph on silica, eluting with 3%MeOH/CH$_2$Cl$_2$ to obtain the title compound as a foam. MS: M+1=349.

EXAMPLE 2

3(S)-[2(S)-ACETYLTHIOMETHYL-3-(2-METHYLPHENYL)PROPIONYL]-AMINO-ε-CAPROLACTAM

Combine 3(S)-amino-:-caprolactam (0.28 g,2.2 mmol), 2(S)-acetylthiomethyl-3-(2-methylphenyl)propionic acid (0.50 g,2.0 mmol) and hydroxybenzotriazole (HOBT) (0.33 g,2.2 mmol) in DMF (10ml). Add 1-(3-dimethylaminopropyl)-3-ethylcarbodiimide hydrochloride (DEC) (0.42 g,2.2 mmol). Stir 18hr, partition between EtOAc and H$_2$O, dry and concentrate. Chromatograph on silica, eluting with diethyl ether (Et$_2$O) to obtain the title compound as a foam,$[\alpha]_D^{26}= -31.3°$ (EtOH).

EXAMPLE 3

3(S)-[2(S)-MERCAPTOMETHYL-3-(2-METHYLPHENYL)PROPIONYL]AMINO-ε-CAPROLACTAM

To a solution of the thioester of Example 2 (0.17 g,0.46 mmol) in MeOH (10 ml), add 1.4 ml 1.0N NaOH. Stir 1 hr, concentrate in vacuo and add 1.4 ml 1.0N HCl. Extract with EtOAc, dry and concentrate to obtain the title compound as a solid, m.p. 98-°103° C.

EXAMPLE 4

3(S)-[2(S)-ACETYLTHIOMETHYL-3-(2-METHYL-PHENYL)PROPIONYL]AMINO-δ-VALEROLACTAM

Prepare 3(S)-amino-δ-valerolactam hydrochloride according to the procedure of *J. Chem. Soc. Dalton Trans.*, 1987, p. 1127. Combine this lactam (0.29 g, 2.0 mmol), 2(S)-acetylthiomethyl-3-(2-methylphenyl)propionic acid (0.50 g, 2.0 mmol), triethylamine (0.03 g, 3.0 mmol), and HOBT (0.30 g, 2.0 mmol) in DMF (20 ml). Add DEC (0.38 g, 2.0 mmol). Stir 18 hr, partition between EtOAc and H$_2$O, dry and concentrate. Chromatograph on silica, eluting with 3% MeOH/CH$_2$Cl$_2$ to obtain the title compound as a foam, $[\alpha]_D^{26} = -28.6°$ (EtOH)

EXAMPLE 5

3(S)-[2(S)-MERCAPTOMETHYL-3-(2-METHYL-PHENYL)PROPIONYL]-AMINO-δ-VALEROLACTAM

To a solution of the thioester of Example 4 (0.30 g, 0.86 mmol) in MeOH (9 ml), add 3.0 ml 1.0N NaOH. Stir 4 hr, concentrate in vacuo and add 3.0 ml 1.0N HCl. Extract with EtOAc, dry and concentrate to obtain the title compound as a foam, $[\alpha]_D^{26} = +46.8°$ (EtOH).

The following formulations exemplify some of the dosage forms of the compositions of this invention. In each, the term "active compound" designates a compound of formula I, preferably 3(S)-[2-(acetylthiomethyl)-3-phenylpropionyl]amino-ε-caprolactam. However, this compound may be replaced by equally effective amounts of other compounds of formula I.

PHARMACEUTICAL DOSAGE FORM EXAMPLES

Example A

| No. | Ingredient | Tablets mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

METHOD OF MANUFACTURE

Mix Item Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 mix for 1-3 minutes. Compress the mixture to appropriate size and weight on a suitable tablet machine.

Example B

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |

-continued

| No. | Ingredient | Capsules mg/capsule | mg/capsule |
|---|---|---|---|
| 4. | Magnesium Stearate NF | 4 | 7 |
|   | TOTAL | 250 | 700 |

METHOD OF MANUFACTURE

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

Example C

| Ingredient | Parenteral Preparation mg/vial | mg/vial |
|---|---|---|
| Active Compound Sterile Powder | 100 | 500 |

For reconstitution add sterile water for injection or bacteriostatic water for injection.

We claim:
1. A compound represented by the formula

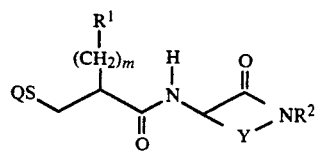

wherein Y is -(CHR$^5$)$_n$-(CR$^3$R$^4$)- or -(CR$^3$R$^4$)$_p$X(CR$^3$R$^4$)$_q$-, wherein two substituents selected from the group consisting of R$^3$, R$^4$ and R$^5$, together with the carbons to which the substituents are attached, when the substituents are present on adjacent carbon atoms, can form a benzene, cyclopentane or cyclohexane ring;

X is -O-, -S-, -SO- or -SO$_2$-;

Q is hydrogen or R$^6$CO-;

m is 1 or 2;

n is 1, 2, 3 or 4;

p is 1 or 2;

q is 2 or 3;

R$^1$ is lower alkyl; aryl, selected from the group consisting of phenyl, naphthyl, substituted phenyl and substituted naphthyl, wherein said substituted phenyl and substituted naphthyl groups are substituted with 1-3 substituents selected from the group consisting of lower alkyl, hydroxy, lower alkoxy, halo, trifluoromethyl, phenyl, phenoxy and phenylthio; heteroaryl or substituted heteroaryl, wherein heteroaryl is selected from the group consisting of furanyl, thienyl, pyrrolyl and pyridyl, and wherein said substituted heteroaryl is substituted with 1-3 substituents selected from the group consisting of lower alkyl, hydroxy, lower alkoxy, halo, trifluoromethyl, phenyl, phenoxy and phenylthio;

R$^2$ is hydrogen, lower alkyl, hydroxylower alkyl, loweralkoxylower alkyl, aryllower alkyl, heteroaryllower alkyl, substituted-aryllower alkyl, or substituted-heteroaryllower alkyl, wherein aryl, heteroaryl, substituted aryl and substituted heteraryl are as defined above;

R$^3$ and R$^4$ are independently hydrogen, lower alkyl, aryllower alkyl, heteroaryllower alkyl, substituted-aryllower alkyl, or substituted-heteroaryllower alkyl, wherein aryl, heteroaryl, substituted aryl and substituted heteroaryl are as defined above;

R$^5$ is hydrogen, lower alkyl, aryllower alkyl, heteroaryllower alkyl, hydroxy, lower alkoxy, mercapto, lower alkylthio, substituted-aryllower alkyl, or substituted-heteroaryllower alkyl, wherein aryl, heteroaryl, substituted aryl and substituted heteroaryl are as defined above; and R$^6$ is lower alkyl, aryl, heteroaryl, wherein aryl, heteroaryl, substituted aryl and substituted heteroaryl are as defined above.

2. A compound of claim 1 wherein Y is -(CHR$^5$)$_n$(CR$^3$R$^4$)-.

3. A compound of claim 2 wherein R$^3$, R$^4$ and R$^5$ are each hydrogen.

4. A compound of claim 3 wherein n is 2 or 3.

5. A compound of claim 1 wherein R$^2$ is hydrogen.

6. A compound of claim 1 wherein R$^1$ is phenyl or lower alkylphenyl and m is 1.

7. A compound of claim 1 wherein Q is hydrogen or acetyl.

8. A compound of claim 1 which is:
3(S)-[2-acetylthiomethyl-3-phenylpropionyl]amino-ε-caprolactam;
3(S)-[2(S)-acetylthiomethyl-3-(2-methylphenyl)propionyl]amino-ε-caprolactam;
3(S)-[2(S)-mercaptomethyl-3-(2-methylphenyl)propionyl]amino-ε-caprolactam;
3(S)-[2(S)-acetylthiomethyl-3-(2-methylphenyl)propionyl]amino-δ-valerolactam;
3(S)-[2(S)-mercaptomethyl-3-(2-methylphenyl)propionyl]amino-δ-valerolactam.

9. A method for treating hypertension or congestive heart failure in mammals comprising administering to a mammal in need of such treatment an effective amount of a compound of claim 1.

10. A pharmaceutical composition comprising an effective amount of a compound of claim 1 in a pharmaceutically acceptable carrier.

* * * * *